United States Patent
Kramer

(10) Patent No.: US 12,239,135 B2
(45) Date of Patent: Mar. 4, 2025

(54) COPPER MICROBE STOPPER

(71) Applicant: Russell Kramer, Sandwich, MA (US)

(72) Inventor: Russell Kramer, Sandwich, MA (US)

( * ) Notice: Subject to any disclaimer, the term of this patent is extended or adjusted under 35 U.S.C. 154(b) by 0 days.

(21) Appl. No.: 17/206,496

(22) Filed: Mar. 19, 2021

(65) Prior Publication Data
US 2022/0167623 A1 Jun. 2, 2022

Related U.S. Application Data

(60) Provisional application No. 63/004,797, filed on Apr. 3, 2020.

(51) Int. Cl.
*A01N 59/20* (2006.01)
*A01N 25/34* (2006.01)
*A61L 15/58* (2006.01)

(52) U.S. Cl.
CPC ............. *A01N 59/20* (2013.01); *A01N 25/34* (2013.01); *A61L 15/58* (2013.01)

(58) Field of Classification Search
CPC ................................ A01N 59/20; A61L 15/58
See application file for complete search history.

(56) References Cited

U.S. PATENT DOCUMENTS

| | | | | |
|---|---|---|---|---|
| 3,960,396 A | * | 6/1976 | Miyahara | E05B 1/0053 16/DIG. 30 |
| 2008/0311322 A1 | * | 12/2008 | Haskin | B32B 27/00 428/35.2 |
| 2016/0317897 A1 | * | 11/2016 | Mariano | B32B 3/30 |
| 2020/0352162 A1 | * | 11/2020 | Karpman | A61L 15/46 |

FOREIGN PATENT DOCUMENTS

| | | | | | |
|---|---|---|---|---|---|
| GB | 1286053 A | * | 5/1971 | | |
| JP | H09324366 | * | 12/1997 | | |
| WO | WO-2008082586 A2 | * | 7/2008 | | A61L 2/03 |

* cited by examiner

*Primary Examiner* — Kyle A Purdy
(74) *Attorney, Agent, or Firm* — Jonathan B. David

(57) ABSTRACT

An embodiment of the invention includes a handle-like mechanism configured to be continuously placed in contact with a plurality of different surfaces. A first copper material placed on an outside surface of the handle-like mechanism to be an intermediary surface between the handle-like mechanism and additional outside surfaces. A portion of the handle-like mechanism is not covered by the first copper material. A second copper material/adhesive is placed over the portion of the handle-like mechanism that is not covered by the first copper material to enable the handle-like mechanism to retain its intended function.

19 Claims, 11 Drawing Sheets

COPPER MICROBE STOPPER

TECHNICAL FIELD

The present disclosure generally relates to providing a copper-based surface microbe stopper on every day times to protect the everyday items from outside contamination from the hands of users and other external surfaces.

BACKGROUND

High contact areas such as buildings typically have doors and stairs that are typically touched by a lot of patrons and objects during the course of a day. As a result, a lot of germs and contaminants from the hands and the objects can get on the doors and stairs.

Due to the germs and contaminants that come into contact with the high touch areas such as the stairs and the doors, many germs are often passed onto various patrons within office buildings or the like. When such germs and contaminants are passed onto patrons, the various patrons can catch viral illnesses such as colds, the flu, and other various ailments caused by the spread of germs and contaminants.

Accordingly, there is a need for high-touch areas to be safe from germs and other contaminants. Moreover, there is a need for high-touch areas to still be frequented and touch by many users without users be at risk to catching germs and contaminants from other uses.

SUMMARY

In an embodiment, a system comprises a handle-like mechanism configured at a fixed position, wherein the handle-like mechanism is configured to be continuously placed in contact with a plurality of different contacts and/or surfaces. The system also includes a first copper material placed on an outside surface of the handle-like mechanism. The copper material is placed around the outside surface of the handle-like mechanism to be an intermediary surface between the handle-like mechanism and additional outside surfaces that attempt to contact with the handle-like mechanism. A portion of the handle-like mechanism is not covered by the copper material to enable the handle-like mechanism to be used for its intended function. The system also includes a second copper material/adhesive placed over the portion of the handle-like mechanism that is not covered by the first copper material. The second copper material/adhesive covers the handle-like mechanism to ensure that an entire portion of the handle-like mechanism is covered with either the first copper material and the second copper material/adhesive, and wherein the handle-like mechanism retains its intended function.

In an embodiment of the system, the intended function function of the handle-like mechanism is to be rotated in one or more directions.

In an an embodiment of the system, wherein the second cooper material/adhesive ensures that no external surfaces contact the handle-like mechanism when the handle-like mechanism is used for its intended function.

In an embodiment of a system, the system includes a stretchable first copper material configured at a first position. The system also includes a handle-like mechanism configured at a second position to be contacted by a plurality of outside surfaces, wherein the handle-like mechanism is configured to be covered with the stretchable copper material. The stretchable copper material covers a portion of the handle-like mechanism to ensure that the outside surfaces do not directly contact the handle-like mechanism, and wherein any handle-like mechanism does not receive any unwanted materials from the outside surfaces. The system also includes a second copper material configured to cover another portion of the handle-like mechanism that is not covered by the first copper material.

In an embodiment of the system, the first cooper material is configured to adapt to a shape of the handle-like mechanism.

In an embodiment of the system, wherein the first cooper material and the second copper material prevent a spread of one or substances from contacting the handle-like mechanism.

In an embodiment of a system, a method includes configuring a handle-like mechanism at a fixed position, wherein the handle-like mechanism is configured to be repeatedly placed in contact with a plurality of different contacts and/or surfaces. The method also includes positioning a first copper material on an outside surface of the handle-like mechanism, wherein the copper material is placed around the outside surface of the handle-like mechanism to be an intermediary surface between the handle-like mechanism and additional outside surfaces that attempt to contact with the handle-like mechanism. A portion of the handle-like mechanism is not covered by the copper material to enable the handle-like mechanism to be used for its intended function. The method also includes configuring a second copper material/adhesive placed over another portion of the handle-like mechanism that is not covered by the first copper material. The second copper material/adhesive covers the handle-like mechanism to ensure that an entire portion of the handle-like mechanism is covered with either the first copper material and the second copper material/adhesive, and wherein the handle-like mechanism retains its intended function.

In an embodiment of the method, wherein the intended function of the handle-like mechanism is to be used as an apparatus for dispersing fluid.

In an embodiment of the method, wherein the intended function of the handle-like mechanism is to provide an opening to a passageway and/or path.

BRIEF DESCRIPTION OF THE FIGURES

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

Figure 1A:
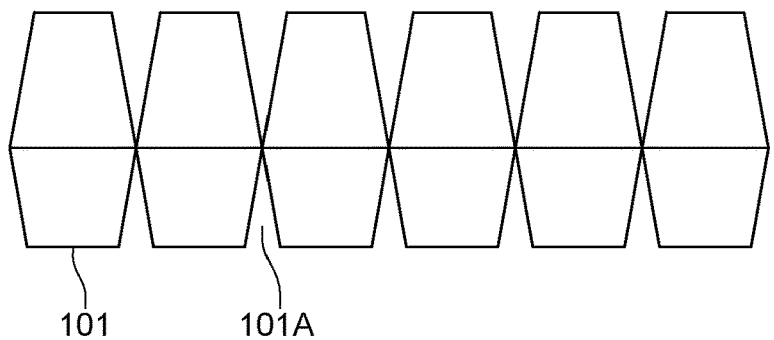
FIGS. 1(A)-(C) illustrates a diagram of copper surface in accordance with an embodiment of the invention.

Unless otherwise indicated illustrations in the figures are not necessarily drawn to scale.

DETAILED DESCRIPTION OF SOME EMBODIMENTS

Background and Context

The particular values and configurations discussed in these non-limiting examples can be varied and are cited merely to illustrate one or more embodiments and are not intended to limit the scope thereof.

Subject matter will now be described more fully herein after with reference to the accompanying drawings, which form a part hereof, and which show, by way of illustration, specific example embodiments. Subject matter may, however, be embodied in a variety of different form and, therefore, covered or claimed subject matter is intended to be construed as not being limited to any example embodiments set forth herein, example embodiments are provided merely to be illustrative. Likewise, a reasonably broad scope for claimed or covered subject matter is intended. Among other issues, subject matter may be embodied as methods, devices, components, or systems. The followed detailed description is, therefore, not intended to be interpreted in a limiting sense.

Throughout the specification and claims, terms may have nuanced meanings suggested or implied in context beyond an explicitly stated meaning. Likewise, phrases such as "in one embodiment" or "in an example embodiment" and variations thereof as utilized herein may not necessarily refer to the same embodiment and the phrase "in another embodiment" or "in another example embodiment" and variations thereof as utilized herein may or may not necessarily refer to a different embodiment. It is intended, for example, that claimed subject matter include combinations of example embodiments in whole or in part.

In general, terminology may be understood, at least in part, from usage in context. For example, terms such as "and," "or," or "and/or" as used herein may include a variety of meanings that may depend, at least in part, upon the context in which such terms are used. Generally, "or" if used to associate a list, such as A, B, or C, is intended to mean A, B, and C, here used in the inclusive sense, as well as A, B, or C, here used in the exclusive sense. IN addition, the term "one or more" as used herein, depending at least in part upon context, may be used to describe any feature, structure, or characteristic in a singular sense or may be used to describe combinations of features, structures, or characteristics in a plural sense. Similarly, terms such as a "a," "an," or "the:, again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

One having ordinary skill in the relevant art will readily recognize the subject matter disclosed herein can be practiced without one or more of the specific details or with other methods. In other instances, well-known structures or operations are not shown in detail to avoid obscuring certain aspects This disclosure is not limited by the illustrated ordering of acts or events, as some acts may occur in different orders and/or concurrently with other acts or events. Furthermore, not all illustrated acts or events are required to implement a methodology in accordance with the embodiments disclosed herein.

Unless defined otherwise, all technical and scientific terms used herein have the same meanings as commonly understood by one of ordinary skill in the art to which the disclosed embodiments belong. Preferred methods, techniques, devices, and materials are described, although any methods, techniques, devices, or materials similar or equivalent to those described herein may be used in the practice or testing of the present invention.

Although claims have been included in this application to specific enumerated combinations of features, it should be understood the scope of the present disclosure also includes any novel feature or any novel combination of features disclosed herein.

References "an embodiment," "example embodiment," "various embodiments," "some embodiments," etc., may indicate that the embodiment(s) so described may include a particular feature, structure, or characteristic, but not every possible embodiment necessarily includes that particular feature, structure, or characteristic.

Headings provided are for convenience and are not to be taken as limiting the present disclosure in any way.

Each term utilized herein is to be given its broadest interpretation given the context in which that term is utilized.

TERMINOLOGY

The following paragraphs provide context for terms found in the present disclosure (including the claims):

The transitional term "comprising", which is synonymous with "including," "containing," or "characterized by," is inclusive or open-ended and does not exclude additional, unrecited elements or method steps. See, e.g., *Mars Inc.* v. *H.J. Heinz Co.*, 377 F.3d 1369, 1376, 71 USPQ2d 1837, 1843 (Fed. Cir. 2004) ("[L]ike the term 'comprising,' the terms 'containing' and 'mixture' are open-ended."). "Configured to" or "operable for" is used to connote structure by indicating that the mechanisms/units/components include structure that performs the task or tasks during operation. "Configured to" may include adapting a manufacturing process to fabricate components that are adapted to implement or perform one or more tasks.

"Based On." As used herein, this term is used to describe factors that affect a determination without otherwise precluding other or additional factors that may affect that determination. More particularly, such a determination may be solely "based on" those factors or based, at least in part, on those factors.

All terms of example language (e.g., including, without limitation, "such as", "like", "for example", "for instance", "similar to", etc.) are not exclusive of other examples and therefore mean "by way of example, and not limitation . . . ".

A description of an embodiment having components in communication with each other does not infer that all enumerated components are needed.

A commercial implementation in accordance with the scope and spirit of the present disclosure may be configured according to the needs of the particular application, whereby any function(s of the teachings related to any described embodiment of the present invention may be suitably changed by those skilled in the art.

The flowchart and block diagrams in the figures illustrate the architecture, functionality, and operation of possible implementations of systems and methods according to various embodiments. Functions noted in the block may occur out of the order noted in the figures. For example, two blocks shown in succession may, in fact, be executed substantially concurrently, or the blocks may sometimes be executed in the reverse order, depending upon the functionality involved.

Further, any sequence of steps that may be described does not necessarily indicate a condition that the steps be performed in that order. Some steps may be performed simultaneously.

The functionality and/or the features of a particular component may be alternatively embodied by one or more other devices that are not explicitly described as having such functionality/features. Also, various embodiments of the present invention need not include a device itself.

More specifically, as will be appreciated by one skilled in the art, aspects of the present invention may be embodied as a system and/or method. Furthermore, aspects of the present invention may take the form of a plurality of systems to enable gas meter to perform self-checking to determine its overall functioning without requiring a meter operator.

Various embodiments of the present invention will be described in detail with reference to the drawings, wherein like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some.

In describing embodiments of the present invention, the following terminology will be used. The singular forms "a," "an," and "the" include plural referents unless the context clearly dictates otherwise.

Introduction

Embodiments of the present invention include one more copper materials configured to be placed on surfaces frequently touched by a plurality of users.

The one or more copper materials can configure to the shape of the surface that they are covering. The copper materials will be an intermediate surface between the covered surface and the outside contacts that attempt to frequently touch the covered surface.

The covered surface can be a handle-like mechanism that is frequently touched by users. The handle-like mechanism can be a door knob, a cup, a wrench, a utility tool, etc. the copper materials can conform to the shape of the specific handle-like mechanism, and protect the handle-like mechanism from any germs or unwanted contaminants of the hands of users that attempt to contact the handle-like mechanism.

System Structure

Figure 1B:
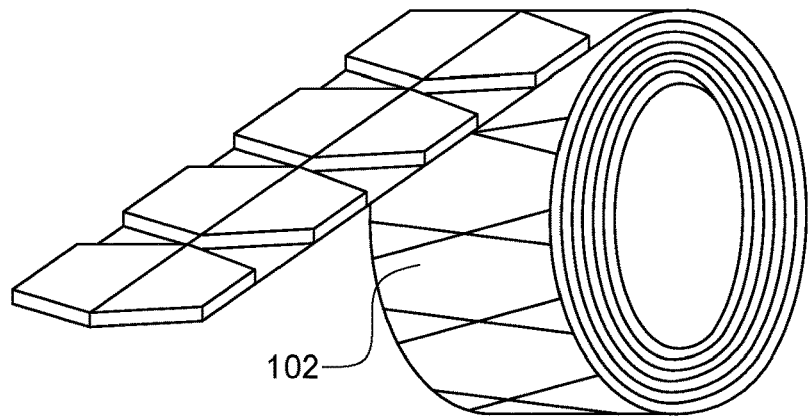
Figure 1C:
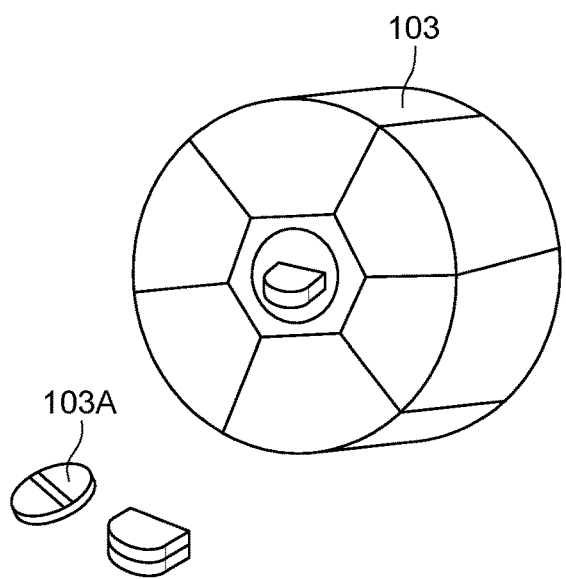

FIGS. 1(A)-(C) illustrate a system where a doorknob is frequently touch by a plurality of users. Many users will contact the doorknob and rotate the door know in order to gain access to path going past the doorknob. To prevent the spread of germs and other contaminants on the doorknob, copper materials are placed on the doorknob to ensure that the contaminants do not come into contact on the doorknob.

Referring to FIGS. 1(A)-(C) illustrate a special type of tape 102 that includes notches 101a removed form tape 101 to create flat templates. The tape 102 with the notches 101a can be used to conform to the doorknob 103 and other irregular surfaces such as coffee cups, table counters, etc. The shape of the notches 101a enables the tape 102 to conform to the shape of the irregular surface such as the doorknob 103. The copper tape 102 can cover a portion of the doorknob 103 to ensure that the hands of users that contact the doorknob 103 do not contact portions of the doorknob 103 and thereby contaminate or pass germs onto the doorknob 103.

In FIGS. 1(A)-(C), a portion of the doorknob 103 can remain uncovered after the copper tape 102 with the notches 101a are used to cover the doorknob 103. As such, a small copper coated tab 103a with an adhesive can be used to cover the uncovered version of the doorknob 103. The small copper coated tab 103a is then placed over the doorknob 103 to enable the doorknob 103 to be covered with the tape 102, notches 101a, and copper coated tab 103a. As such no outside surfaces such as the hands of users can contact the doorknob 103 during regular and routine use of the doorknob 103, and also contaminate the doorknob 103 with germs, viruses, etc.

Figure 2A:
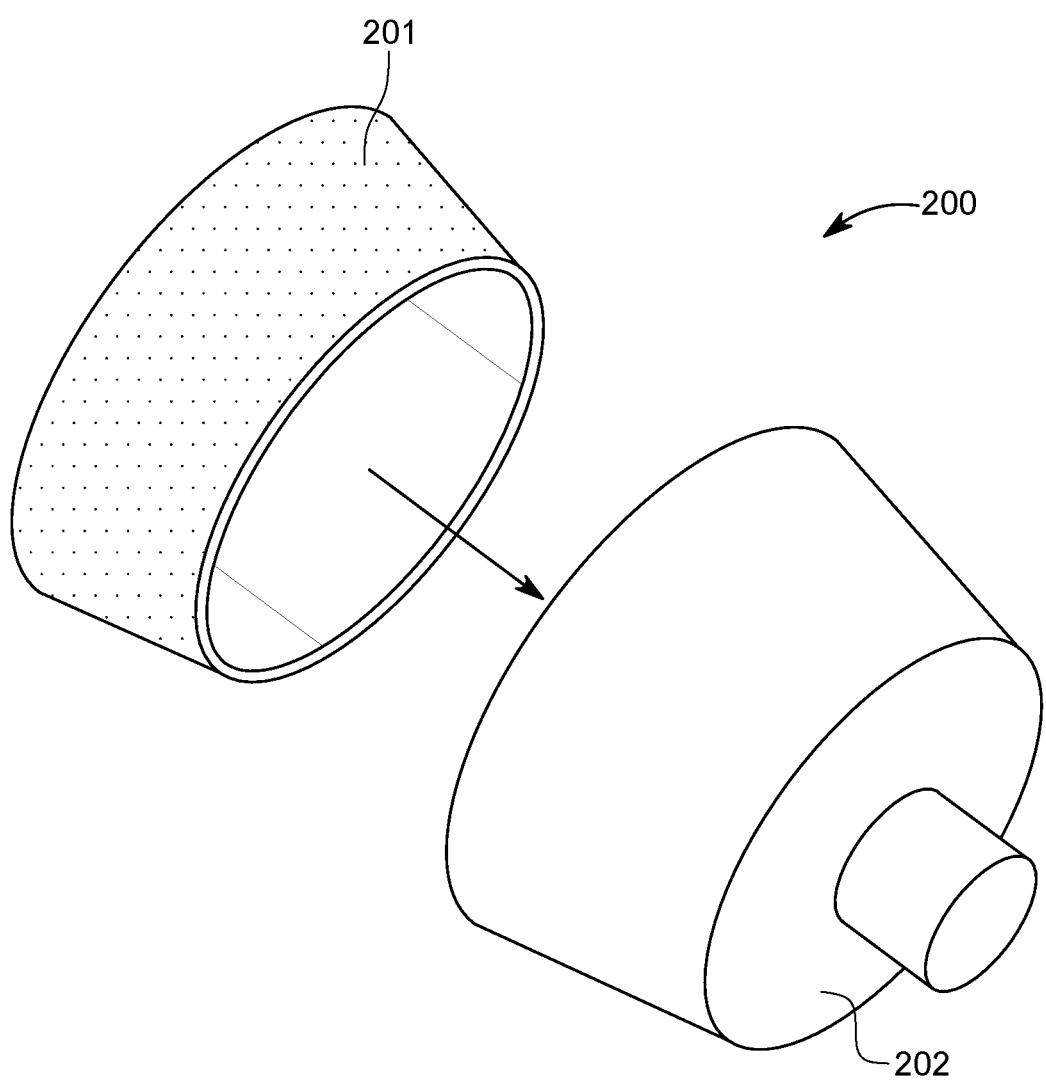
FIGS. 2(A)-(C) illustrate diagrams of copper being placed around a cup.
Figure 2B:
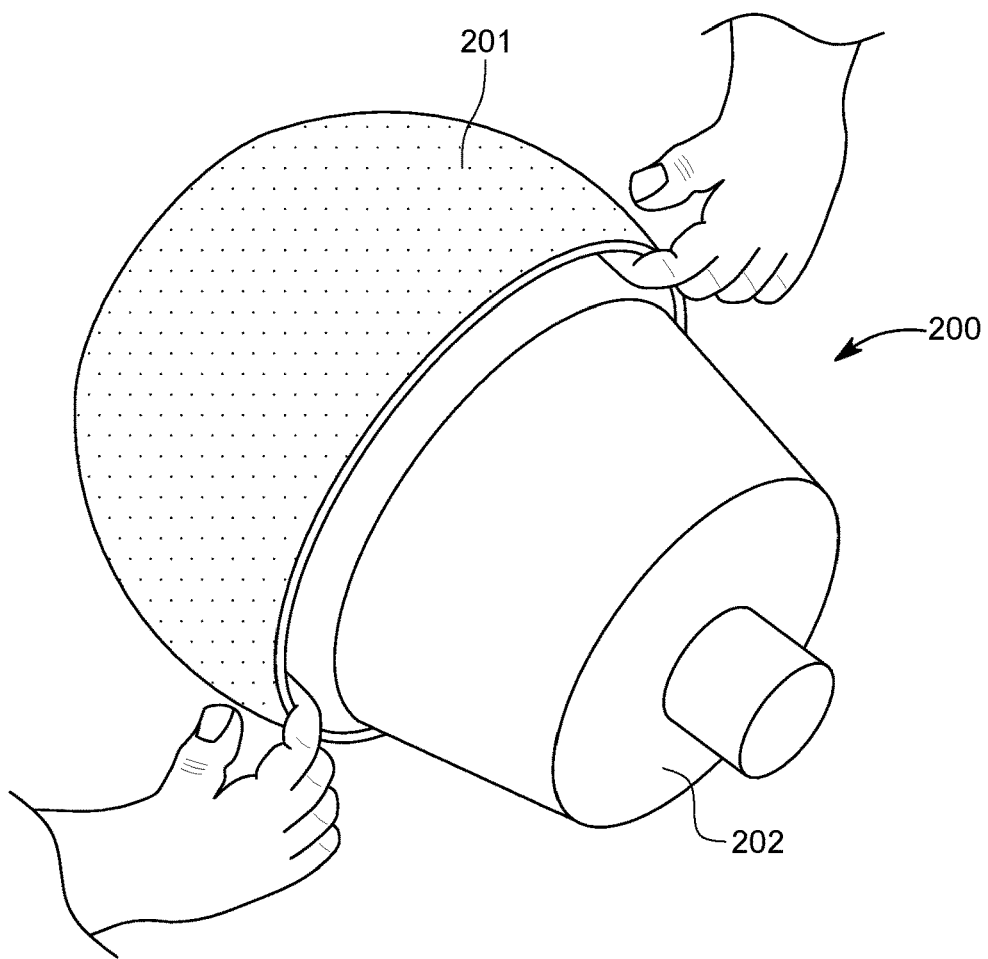
Figure 2C:
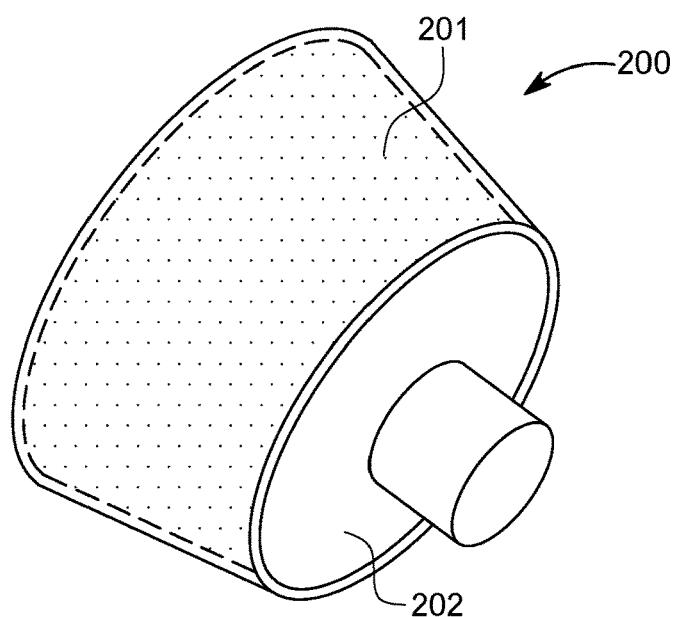

FIGS. 2(A)-(C) illustrates how copper material is placed around the surface of a cup to protect the cup from unwanted contamination from the hands of multiple users. In FIGS. 2(A)-(C), a system 200 with a copper material 201 is illustrated. The copper material 201 is stretchable and is able to attach to various shaped surfaces. The copper material 201 can include latex, rubber, nylon, spandex, and other similar stretching material that can enable the copper material 201 to conform to the shape of many different types of items.

In FIGS. 2(A)-2(C), a cup 202 is illustrated. The cup 202 can be used by a plurality of users on a consistent basis. Without any covering, many different germs and contaminants can contact the cup 202 and thereby contaminate the cup 202. The copper material 201 can be placed around the cup 202 to protect the cup 202 from outside contamination from one or more hands or other outside surfaces. As the copper material 201 is fully placed around the cup 202, the cup 202 is protected from outside contaminants that one or more users' hands or objects can contain.

Figure 3:
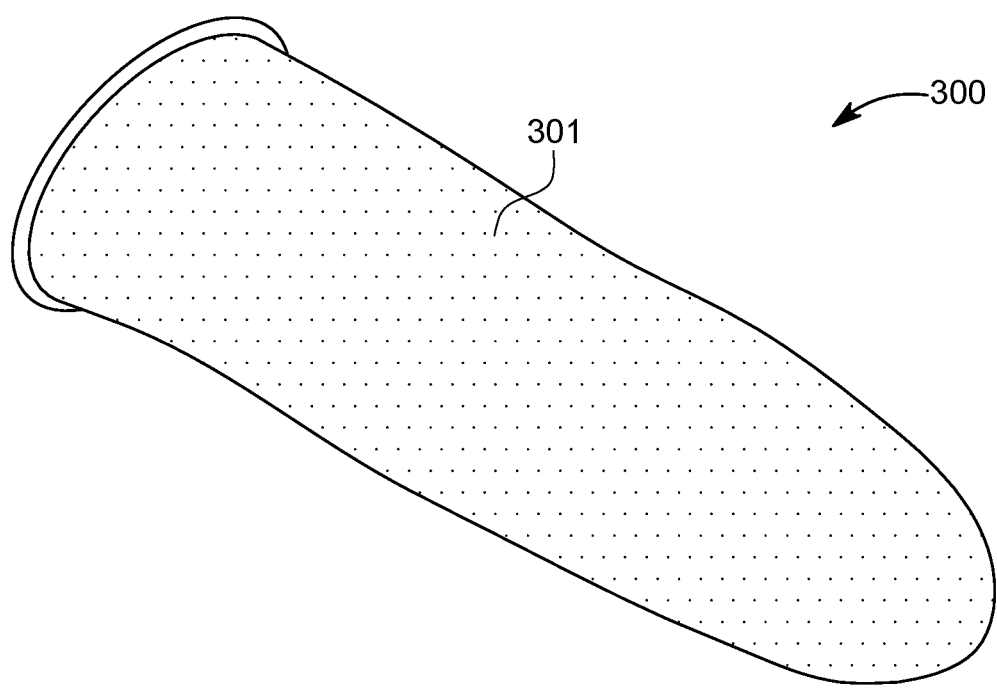
FIG. 3 illustrates a copper material n accordance with an embodiment of the invention.

In FIG. 3, another embodiment is illustrated. Another article of manufacture is illustrated. An organ 300 in an elongated form is shown. The organ 300 can come in various shapes and sizes. A copper material 301 in stretchable form can be placed over the organ 300. When the copper material 301 covers the organ 300, the organ 300 can be protected during physical activities. As such, the organ 300 can be protected from various viruses and sexually transmitted diseases as no outside organs can come into direct contact with the organ 300 while the organ 300 is covered with the copper material 301.

Figure 4:
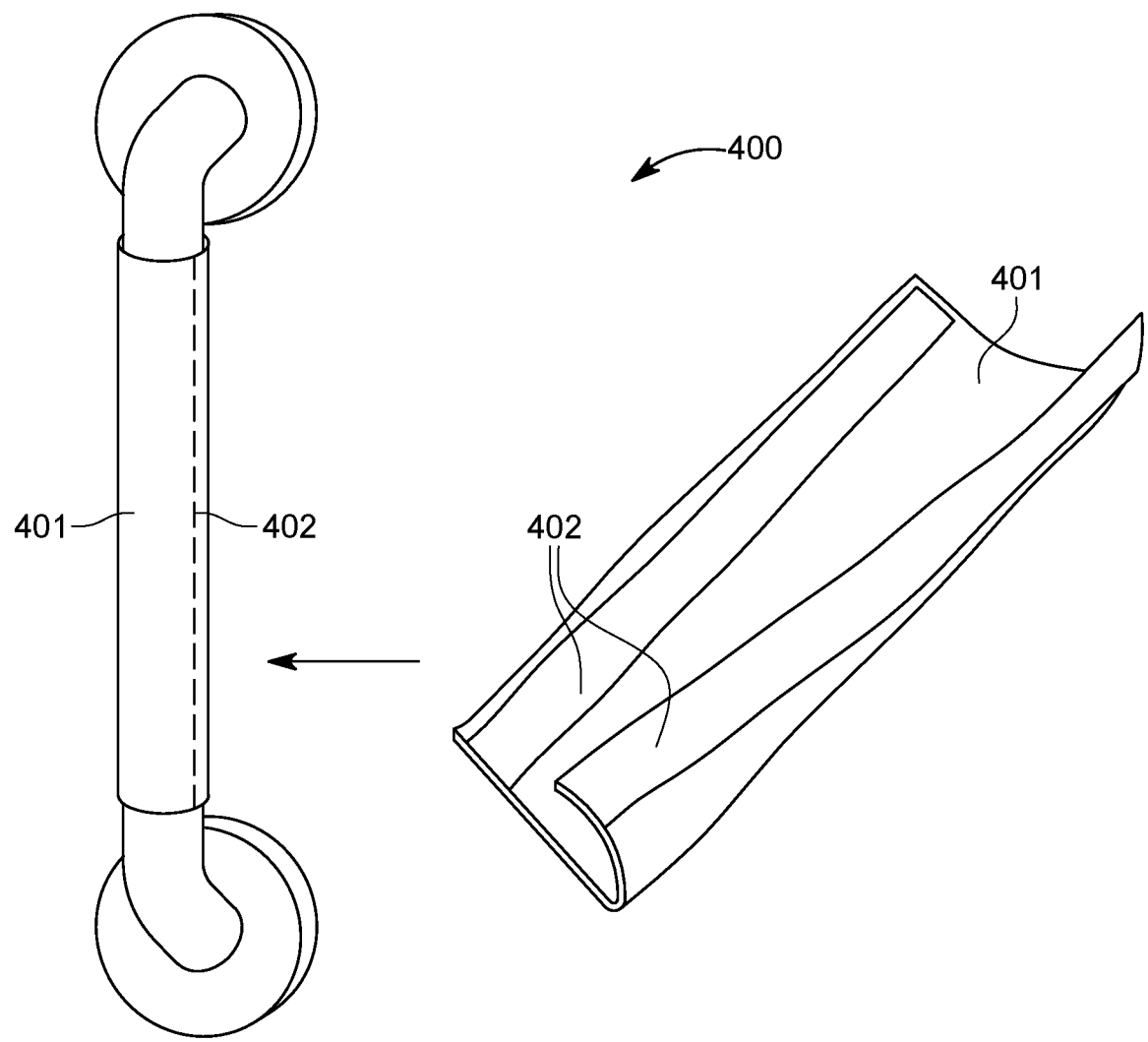
FIG. 4 illustrates an elongated surface being protected by copper material in accordance with an embodiment of the invention.

FIG. 4 illustrates another example of copper material with adhesives protecting an elongated surface. A system is illustrated with railing/pole 400 is showing. Multiple users can grab a hold of the railing/pole 400 on multiple occasions during its use during the day. As such, many germs and contaminants can be on the railing/pole 400. Stretchable copper material 401 with an adhesive 402 can be placed around the railing/pole 400 to cover the railing/pole 400. The adhesive 402 can be in the form of stripes on opposing edges or uniformly applied to the entire inner surface of the railing/pole 400. The copper material 401 with the adhesive 402 provides a snug fit around the railing/pole 400. When the copper material 401 with the adhesive 402 is placed around the railing/pole 400, the mostly commonly used portion of the railing/pole 400 is protected. As such, multiple users grabbling the common area of the railing/pole 400 cannot cause any contamination onto the railing/pole 400. As such, all of the users that use the railing/pole 400 throughout the course of a day will be protected from contacting various germs/contaminants, etc.

Figure 5A:
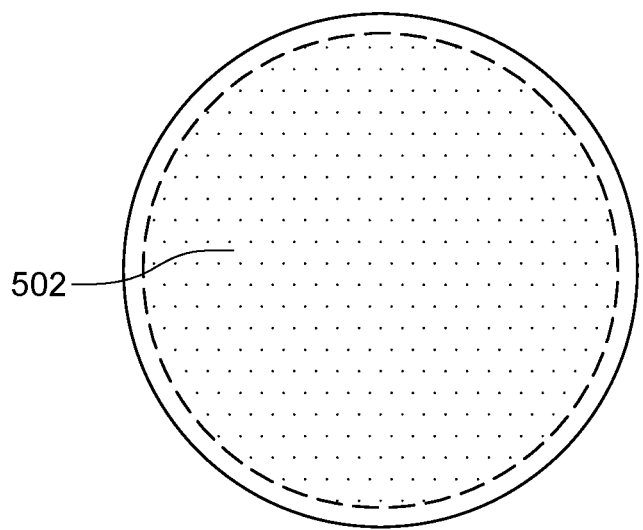
FIGS. 5(A)-(C) illustrate that stretchable copper material can fit around different shapes and sizes in accordance with an embodiment of the invention.
Figure 5B:
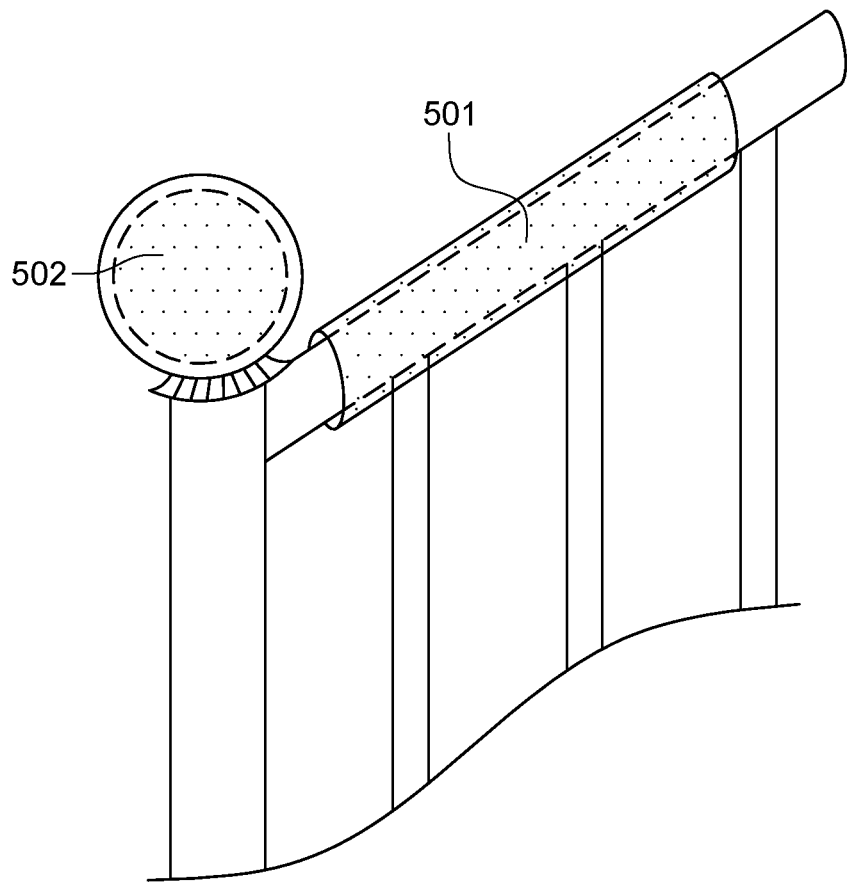
Figure 5C:
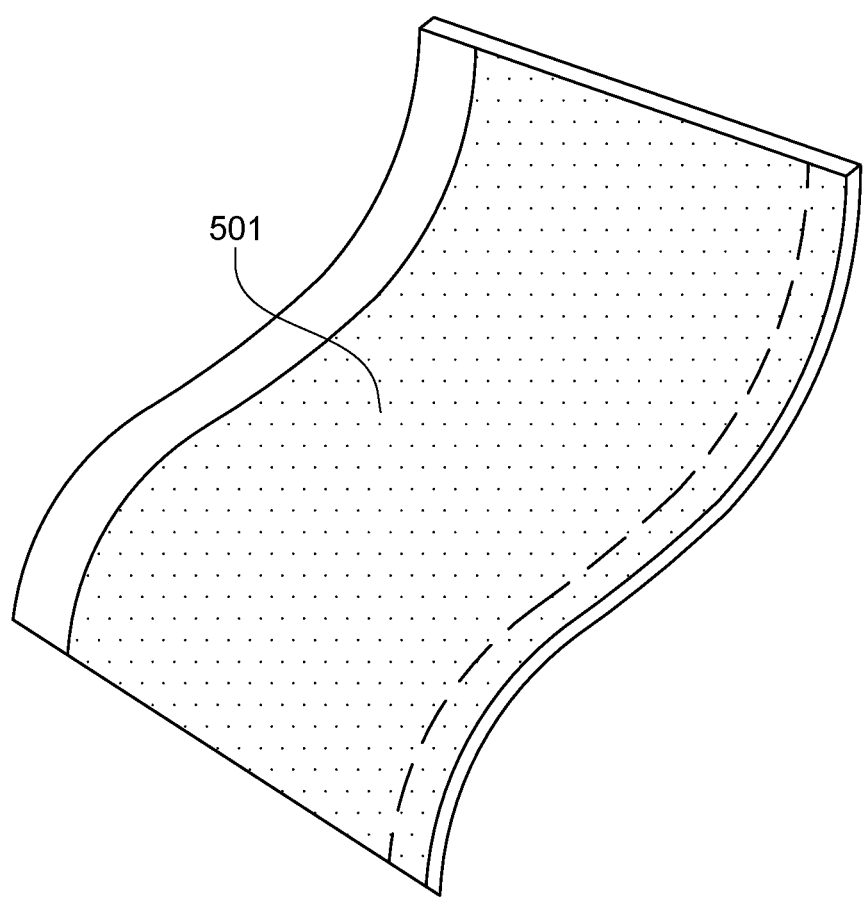

In FIGS. 5(A)-(C) illustrate how the copper surface includes stretchable materials in the form of rectangles and circles. A stair railing 500 is illustrated. Copper material 501 can be placed over the railing of the stairs 500. The copper material 502 can be placed over the pole. The copper materials 501, 502 show that they can conform to a circle and rectangle respectively. The stretchable copper materials 501, 502 with adhesives can protect a stair railing 500 with a railing and pole from outside germs, contaminants, and viruses from the hands of various users.

Figure 6A:
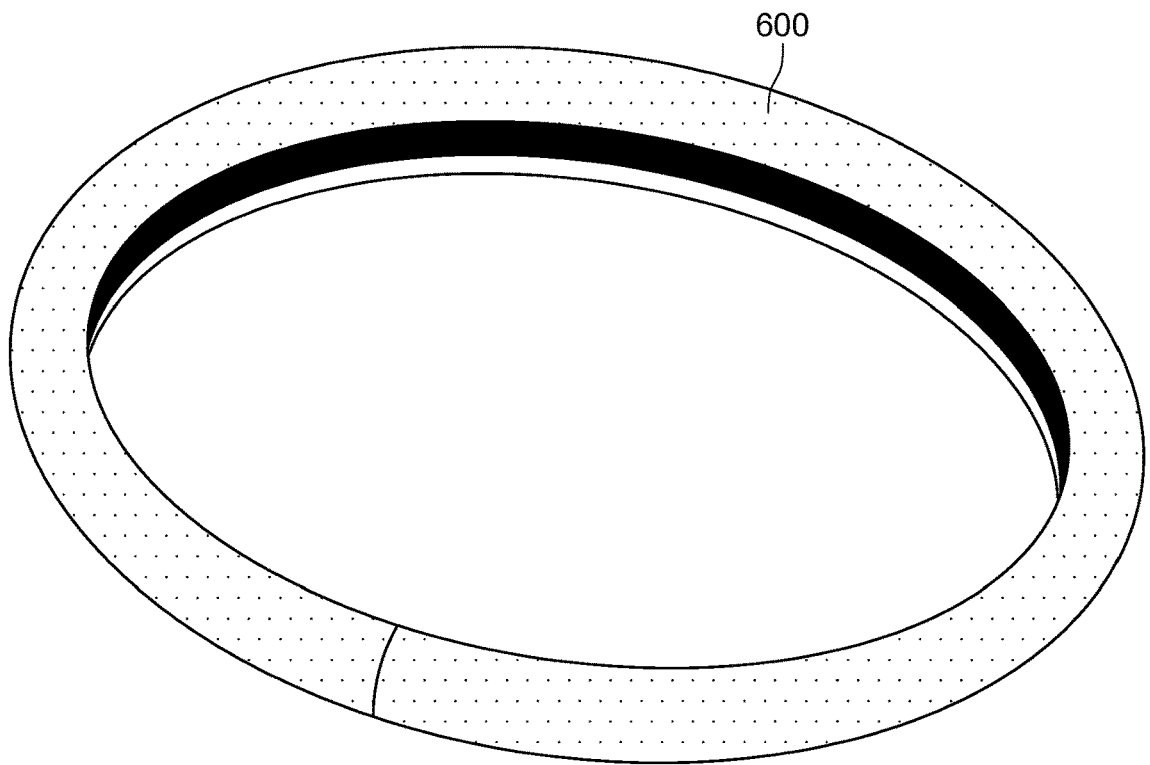
FIGS. 6(A)-(B) illustrate how the copper material can fit around circular objects.

Referring to FIG. 6(A), a circular object such as a steering cover can be covered by a copper material 600 with an adhesive that can repeal germs and contaminants. Users frequently touch the outer edges of the steering cover on many occasions. The copper material 600 is stretchable, to where the copper material 600 can easily fit around the circumference of the steering cover. The copper material 600 on the outer edge of the steering cover will protect the steeling cover from any contaminants and germs that users' hands typically carry. In addition, any external outside surfaces such as contaminated keys, or other objects will not be able to contaminate the steering cover in any way possible.

Figure 6B:
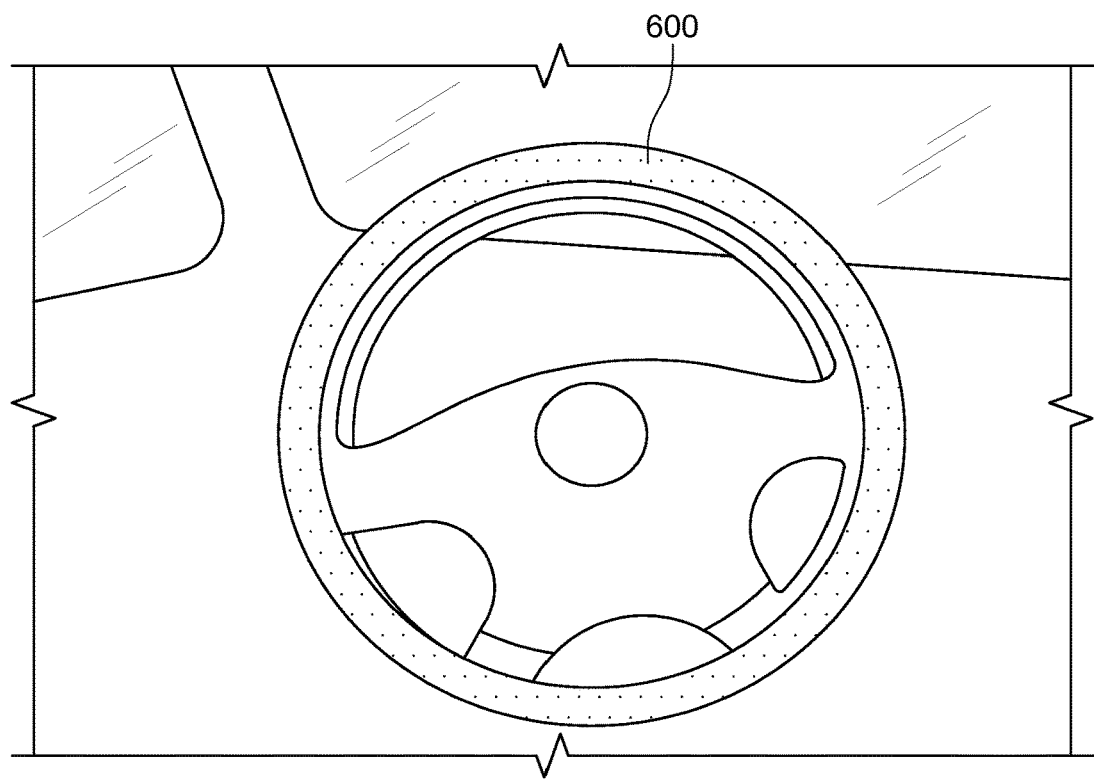

In FIG. 6(B), the steering wheel of a vehicle is shown. On many occasions, the multiple users of the same vehicle can use the steering wheel to drive the car or even a public bus. To avoid the unnecessary exchange of germs and viruses, material can be placed on the steering wheel to protect the steering wheel from the germs and viruses that can be found on the hands of viruses. The stretchable copper material 600 with an adhesive can prevent outside germs or viruses from coming into contact with the steering wheel when the vehicle is driven. The stretchable copper material 600 with the adhesive can protect the steering wheel for as long as needed when multiple users drive the vehicle. As such, the spread of germs of viruses due to different hands and surfaces coming into contact with the steering wheel is prevented.

Figure 7A:
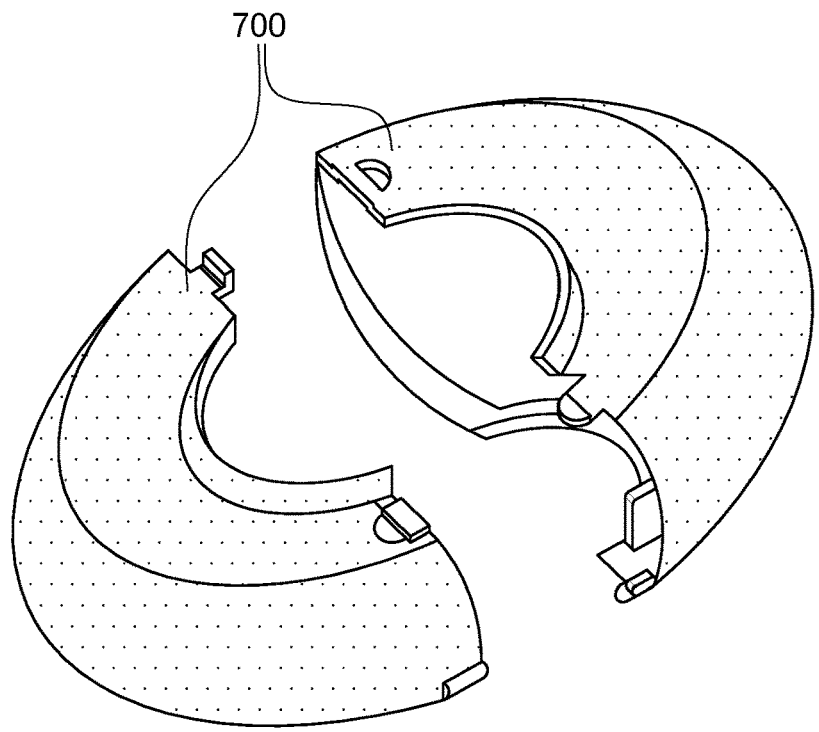
FIG. 7(A)-(B) illustrate two halves of a door knob cover in accordance with an embodiment of the invention.

Referring to FIG. 7(A) illustrates two halves of a copper microbe stopper doorknob cover (doorknob cover) 700. The doorknob cover 700 is designed to securely fit around a standard doorknob that is typically found in high contact areas in office buildings or the like. The doorknob cover 700, when placed around doorknobs, can protect the doorknobs from contamination by the hands of various users. In addition, contamination from various objects that accidentally contact the doorknobs can be prevented. The doorknob cover 700 will ensure that no portion of the doorknobs come into contact with the hands of users, or into contact with various objects.

Figure 7B:
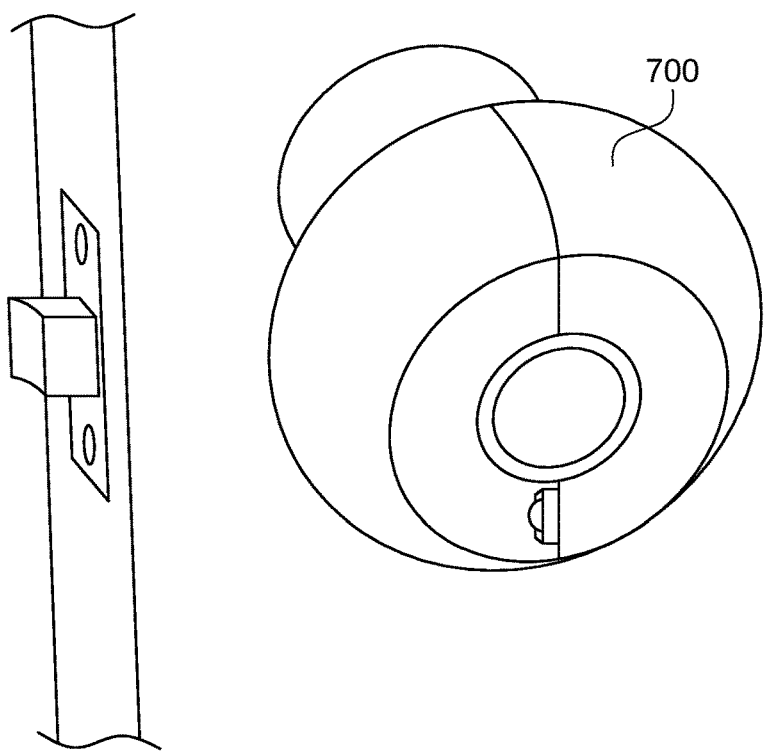

FIG. 7(B) illustrates the doorknob cover 700 secured over a doorknob. When secured over the doorknob, the doorknob cover 700 ensures that no portion of the doorknob is exposed to outside hands or objects that frequently come into contact with the doorknob during the course of a typical day. As a result, the possibility of germs and other contaminants come into contact with the doorknob is greatly prevented. The doorknob cover 700 can also last for as long as required. The doorknob cover 700 will not erode and lose effectiveness due to the frequent touching by hands and/or objects. Consequently, the doorknob cover 700 can ensure that the doorknob will not receive any unwanted contaminants or germs that cause the spread of germs and diseases.

Figure 8:
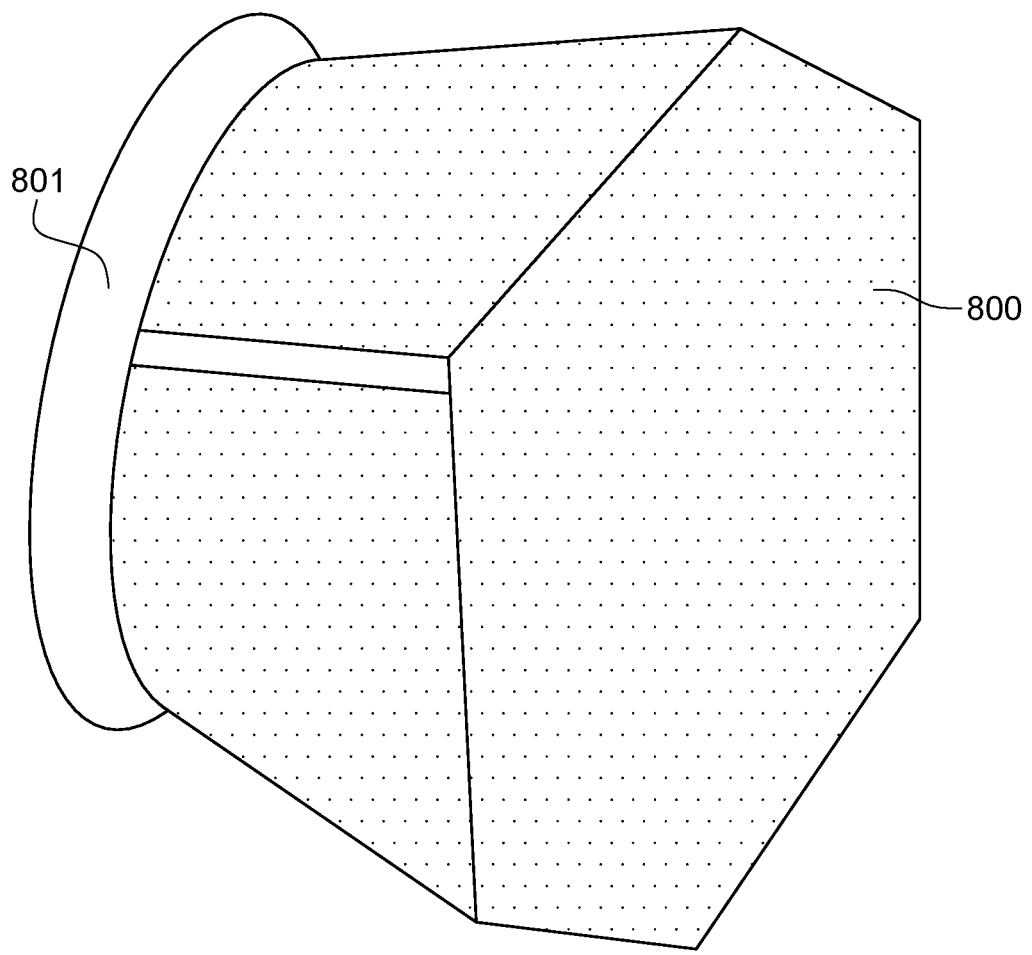
FIG. 8 illustrates a copper material and stretchable elastic band in accordance with an embodiment of the invention.

In FIG. 8, a copper material 800 stretches around the doorknob, while a stretchable elastic band 801 stretches around the doorknob and resides over the stem of the door. The copper material 800 covers the entire circumference of the doorknob. As in FIG. 7, the copper material 800 protects the doorknob from the multitude of hands that will repeatedly use the doorknob to get to one or more places within a building or location. The copper material 800 also protects the door from the multitude of objects that repeatedly bump into the doorknob by users carrying the objects within the building or location. The stretchable elastic band 801 can protect the stem of the doorknob from the hands and/or objects that will inevitably contact the stem portion of the doorknob. Both the copper material 800 and the stretchable elastic band 801 can ensure that the entire portion of the doorknob is completely covered. Consequently, no portion of the doorknob will come into contact with the various hands and objects that will typically contact the doorknob. As a result, the spread of germs, contaminants, and diseases can be prevented as a result.

Figure 9A:
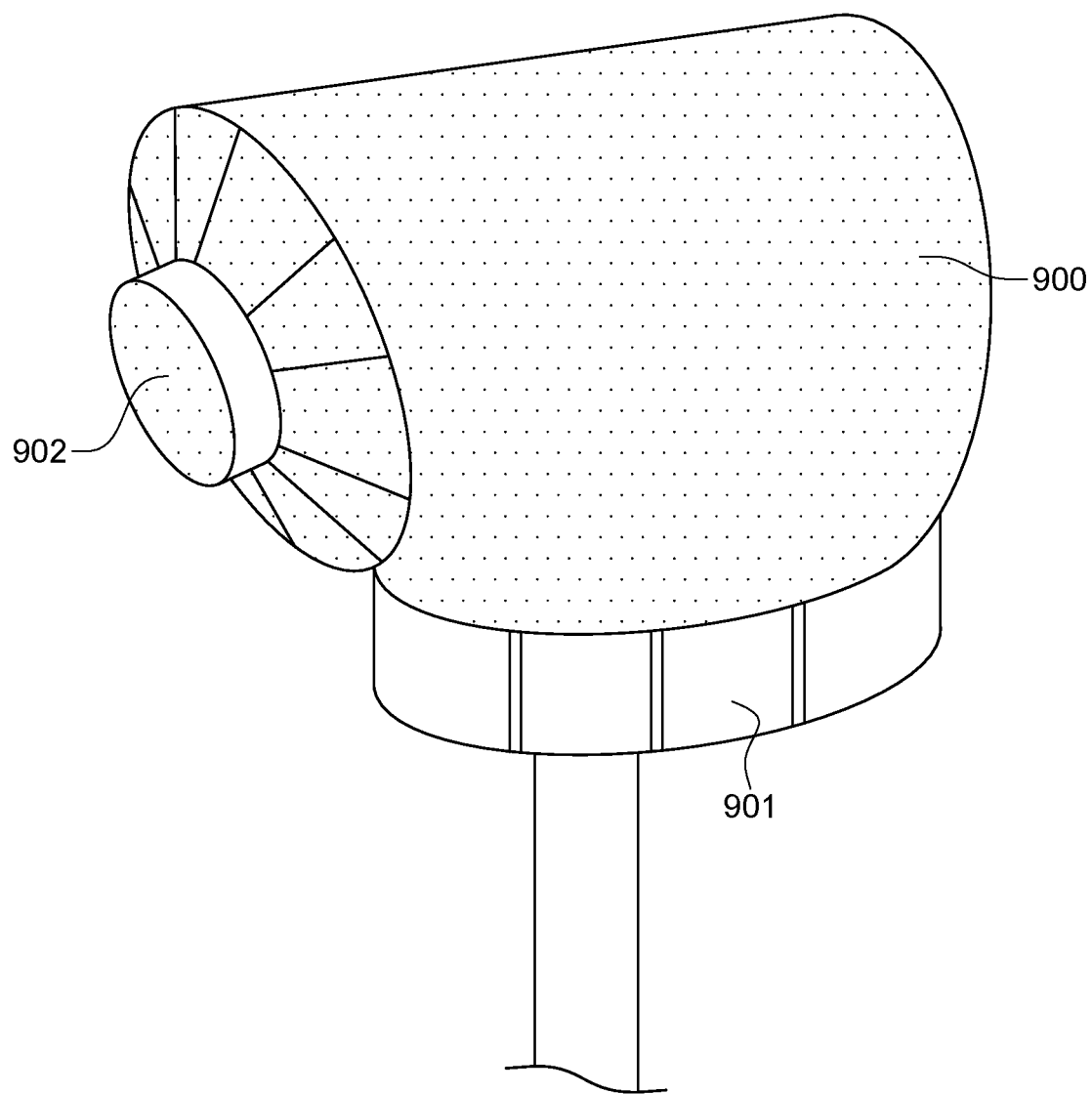
FIGS. 9(A)-(B) illustrate copper material and elastic band to cover a stick shift in an automobile in accordance with an embodiment of the invention.
Figure 9B:
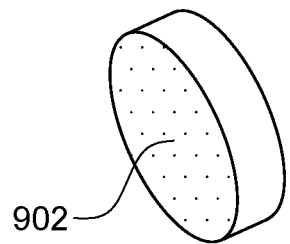

FIGS. 9(A)-(B) illustrate the copper material covering a stick shift that can typically be found in a car or a truck. Many cars and trucks can often be configured with stick shift handles. More than one driver often drives such cars and trucks that are configured with stick shift handles. As a result, germs can be spread through the frequent touching of the stick shift handle among family members and friends that use the car/truck configured with the stick shift handle.

In FIGS. 9(A)-(B), stretchable copper material 900 is placed around the circumference of the stick shift handle to ensure that the any portion of that stick shift handle that is touched by the multiple drivers prevents any hand with potential germs or contaminants from touching that portion of the stick shift handle. A stretchable elastic band 901 can fit around the stem of the stick shift handle. The stretchable elastic band 901 ensures that the stem of the stick shift handle will not be contacted by the hands of any of the drivers or the passengers. As such, no germs/contaminants from the hands of the drivers will get onto the stem of the stick shift handle. In addition, the stick shift handle can have a button/knob that allows the driver to shift gears within the car/truck. The knob can be on the side of the stick shift lever. Copper material 902 can be placed to cover the knob of the stick shift lever. As a result, when changing gears, the knob will also not be contaminated by the hands of the drivers due to the copper material 902 covering the knob.

Those skilled in the art will appreciate that the example embodiments are non-exhaustive and that embodiments other than that described here may be included without departing from the scope and spirit of the presently disclosed embodiments.

Advantages

The copper stretched material is configurable to be placed over high traffic contact points. Such contact points can include doorknobs that lead to various walkways and passageways. Other high contact points can include stairwells in which people travel up the stairs. Still other high contact points can include coffee cups which people use often in their homes. The copper stretchable materials can fit around these high traffic points to protect the door knobs, stair wells, and coffee cups from the hands of users that may otherwise contaminate those areas.

The copper materials can also protect reproductive organs. The copper material is stretchable enough to fit around a reproductive organ and protect the organ from various bodily fluids that can lead to sexually transmitted diseases or the like. Accordingly, if needed, users can use the copper material to protect themselves from sexually transmitted diseases.

Yet another advantage is that steering covers and steering wheels can be covered with the copper material. Steering wheels and steering covers can be found in various vehicles such as buses. Buses can have a high traffic of people that cone into contact with the steering cover and steering wheel. In addition, more than one driver may drive the bus. To protect the steering wheel and cover, the copper material can fit comfortably around both the steering wheel and cover to protect both the steering wheel and over. As a result, both the steering wheel and cover are protected from the contamination and germs from various hands that can come into contact with both the steering cover and wheel.

Conclusion

All references, including granted patents and patent application publications, referred herein are incorporated herein by reference in their entirety.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Various aspects of the invention have been described above by way of illustration, and the specific embodiments disclosed are not intended to limit the invention to the particular forms disclosed. The particular implementation of the system provided thereof may vary depending upon the particular context or application. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

The corresponding structures, materials, acts, and equivalents of all means or step plus function elements in the claims below are intended to include any structure, material, or act for performing the function in combination with other claimed elements as specifically claimed.

The invention claimed is:

1. A system comprising:
   a handle-like mechanism configured at a fixed position, wherein the handle-like mechanism is configured to be continuously placed in contact with a plurality of different contacts and/or surfaces;
   a first copper material placed on an outside surface of the handle-like mechanism, wherein the copper material is placed around the outside surface of the handle-like mechanism to be an intermediary surface between the handle-like mechanism and additional outside surfaces that attempt to contact with the handle-like mechanism, wherein a portion of the handle-like mechanism is not covered by the copper material to enable the handle-like mechanism to be used for its intended function; and
   a second copper material comprising an adhesive, the second copper material being placed over the portion of the handle-like mechanism that is not covered by the first copper material, wherein the second copper material covers the handle-like mechanism to ensure that an entire portion of the handle-like mechanism is covered with the first copper material and the second copper material, wherein the handle-like mechanism retains its intended function, wherein a top and bottom portion of the second copper material is connected to a top and bottom portion of the first copper material to collectively cover an entire circumference of the handle-like mechanism, wherein the handle-like mechanism is one of a bodily organ or cup, and wherein the first copper material and the second copper material are stretchable material not internally affixed to the handle-like mechanism, wherein the stretchable material is configured to be affixed on the handle-like mechanism in a shape of the bodily organ or cup, and wherein the handle-like mechanism is configured to engage in sexual intercourse.

2. The system of claim 1, wherein the intended function of the handle-like mechanism is to be rotated in one or more directions.

3. The system of claim 1, wherein the intended function of the handle-like mechanism is to be pulled by a plurality of different exterior surfaces.

4. The system of claim 1, wherein handle-like mechanism is a doorknob.

5. The system of claim 1, wherein the handle-like mechanism is a cup.

6. The system of claim 1, wherein the first copper material is in a form of circles and/or rectangles.

7. A system comprising:
   a stretchable first copper material configured at a first position;
   a handle-like mechanism configured at a second position to be contacted by a plurality of outside surfaces, wherein the handle-like mechanism is configured to be covered with the stretchable copper material, wherein the stretchable copper material covers a portion of the handle-like mechanism to ensure that the outside surfaces do not directly contact the handle-like mechanism, and wherein any handle-like mechanism does not receive any unwanted materials from the outside surfaces; and
   a second copper material comprising an adhesive, the second copper material configured to cover another portion of the handle-like mechanism that is not covered by the first copper material, wherein a top and bottom portion of the second copper material is connected to a top and bottom portion of the first copper material to collectively cover an entire circumference of the handle-like mechanism, wherein the handle-like mechanism is one of a bodily organ or cup, and wherein the first copper material and the second copper material are stretchable material not internally affixed to the handle-like mechanism, wherein the stretchable material is configured to be affixed on the handle-like mechanism in a shape of the bodily organ or cup, and wherein the handle-like mechanism is configured to engage in sexual intercourse.

8. The system of claim 7, wherein the handle-like mechanism is continuously rotated.

9. The system of claim 7, the first copper material is configured to adapt to a shape of the handle-like mechanism.

10. The system of claim 7, wherein the handle-like mechanism is moved in a horizontal and/or vertical direction.

11. The system of claim 7, wherein the second copper material is configured with an adhesive to prevent the outside surfaces from contacting the handle-like mechanism.

12. The system of claim 11, wherein the adhesive is configured to a shape of the handle-like mechanism.

13. The system of claim 7, wherein the first copper material and the second copper material prevent a spread of one or more substances from contacting the handle-like mechanism.

14. A method comprising:
configuring a handle-like mechanism at a fixed position, wherein the handle-like mechanism is configured to be repeatedly placed in contact with a plurality of different contacts and/or surfaces;
positioning a first copper material on an outside surface of the handle-like mechanism, wherein the copper material is placed around the outside surface of the handle-like mechanism to be an intermediary surface between the handle-like mechanism and additional outside surfaces that attempt to contact with the handle-like mechanism, wherein a portion of the handle-like mechanism is not covered by the copper material to enable the handle-like mechanism to be used for its intended function; and
configuring a second copper material comprising an adhesive to be placed over another portion of the handle-like mechanism that is not covered by the first copper material, wherein the second copper material/adhesive covers the handle-like mechanism to ensure that an entire portion of the handle-like mechanism is covered with the first copper material and the second copper material, and the wherein the handle-like mechanism retains its intended function, wherein a top and bottom portion of the second copper material is connected to a top and bottom portion of the first copper material to collectively cover an entire circumference of the handle-like mechanism, wherein the handle-like mechanism is one of a bodily organ or cup, and wherein the first copper material and the second copper material are stretchable material not internally affixed to the handle-like mechanism, wherein the stretchable material is configured to be affixed on the handle-like mechanism in a shape of the bodily organ or cup, and wherein the handle-like mechanism is configured to engage in sexual intercourse.

15. The method of claim 14, wherein the second copper material/adhesive prevents unwanted substances and viruses from contacting the handle-like mechanism.

16. The method of claim 14, wherein the first copper material is configured to remove or erase unwanted substances or viruses that contact the first copper material.

17. The method of claim 14, wherein the one or more outside surfaces repeatedly attempt to contact the handle-like mechanism.

18. The method of claim 14, wherein the intended function of the handle-like mechanism is to be used as an apparatus for dispersing fluid.

19. The method of claim 14, wherein the intended function of the handle-like mechanism is to provide an opening to a passageway and/or path.

* * * * *